(12) United States Patent
Lim

(10) Patent No.: US 7,611,517 B2
(45) Date of Patent: Nov. 3, 2009

(54) ROD REDUCER

(75) Inventor: Roy K. Lim, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 974 days.

(21) Appl. No.: 10/789,610

(22) Filed: Feb. 27, 2004

(65) Prior Publication Data

US 2005/0192587 A1    Sep. 1, 2005

(51) Int. Cl.
*A61F 5/00* (2006.01)
(52) U.S. Cl. .................................. 606/86 A
(58) Field of Classification Search .................. 606/61, 606/86, 87, 99, 104, 105, 93, 205–208, 246, 606/279, 86 A, 86 B, 280–299, 914, 915, 606/902–906; 128/69, 20
See application file for complete search history.

(56) References Cited

U.S. PATENT DOCUMENTS

| | | | |
|---|---|---|---|
| 2,681,807 A * | 6/1954 | Krafft | 279/29 |
| 3,604,487 A | 9/1971 | Gilbert | |
| 3,661,187 A | 5/1972 | Caveney et al. | |
| 3,844,291 A | 10/1974 | Moen | |
| 4,050,464 A | 9/1977 | Hall | |
| 4,411,259 A | 10/1983 | Drummond | |
| 4,793,385 A | 12/1988 | Dyer et al. | |
| 5,020,519 A | 6/1991 | Hayes et al. | |
| 5,113,685 A | 5/1992 | Asher et al. | |
| 5,273,519 A * | 12/1993 | Koros et al. | 606/83 |
| 5,282,806 A * | 2/1994 | Haber et al. | 606/139 |
| 5,314,424 A * | 5/1994 | Nicholas | 606/41 |
| 5,314,431 A | 5/1994 | Graziano | |
| 5,330,472 A | 7/1994 | Metz-Stavenhagen | |
| 5,364,397 A | 11/1994 | Hayes et al. | |
| 5,389,099 A | 2/1995 | Hartmeister et al. | |

(Continued)

FOREIGN PATENT DOCUMENTS

DE    42 38 339 A1    5/1994

(Continued)

OTHER PUBLICATIONS

*Compact CD Low Back Surgeon's Documentation*, Sofamor Spine Division, pp. 60-61, 78-79.

(Continued)

*Primary Examiner*—Thomas C Barrett
*Assistant Examiner*—James L Swiger

(57) ABSTRACT

An instrument is provided for use in orthopedic surgery, such as for reduction of spinal rods. In one embodiment, a shaft is pivotably connected to a plate with an aperture, and a sleeve is slidable over the shaft and plate. A base member can be provided for ease in handling the instrument, which may include a ratchet mechanism connected to the sleeve. The plate is moved so that its aperture is oriented to allow an orthopedic implant, such as a Schanz-type screw, to be inserted into the aperture. After insertion, the shaft is moved so as to pivot the plate so that the plate grips or holds the implant. The sleeve is then slid over the shaft, plate and implant in contact with an elongated member, such as a spinal rod, or other implanted device or tissue. Further sliding the sleeve forces the elongated member toward or past the implant.

58 Claims, 9 Drawing Sheets

U.S. PATENT DOCUMENTS

| | | | |
|---|---|---|---|
| 5,423,855 A | 6/1995 | Marienne | |
| 5,449,361 A | 9/1995 | Preissman | |
| 5,451,227 A * | 9/1995 | Michaelson | 606/83 |
| 5,458,608 A | 10/1995 | Wortrich | |
| 5,466,243 A | 11/1995 | Schmieding et al. | |
| 5,484,441 A | 1/1996 | Koros et al. | |
| 5,507,772 A * | 4/1996 | Shutt et al. | 606/205 |
| 5,584,839 A | 12/1996 | Gieringer | |
| 5,591,167 A | 1/1997 | Laurain et al. | |
| 5,616,143 A | 4/1997 | Schlapfer et al. | |
| 5,626,608 A * | 5/1997 | Cuny et al. | 606/205 |
| 5,702,408 A * | 12/1997 | Wales et al. | 606/139 |
| 5,720,751 A | 2/1998 | Jackson | |
| 5,782,830 A | 7/1998 | Farris | |
| 5,851,214 A * | 12/1998 | Larsen et al. | 606/170 |
| 5,899,901 A | 5/1999 | Middleton | |
| 5,910,141 A | 6/1999 | Morrison et al. | |
| 5,944,720 A | 8/1999 | Lipton | |
| 5,961,531 A * | 10/1999 | Weber et al. | 606/167 |
| 6,036,692 A | 3/2000 | Burel et al. | |
| 6,042,582 A | 3/2000 | Ray | |
| 6,063,088 A | 5/2000 | Winslow | |
| 6,126,674 A * | 10/2000 | Janzen | 606/206 |
| 6,146,386 A | 11/2000 | Blackman et al. | |
| 6,322,579 B1 * | 11/2001 | Muller | 606/205 |
| 6,440,133 B1 | 8/2002 | Beale et al. | |
| 6,520,979 B1 * | 2/2003 | Loubens et al. | 606/205 |
| 6,547,805 B1 * | 4/2003 | Loubens et al. | 606/206 |
| 6,648,888 B1 | 11/2003 | Shluzas | |
| 6,660,006 B2 | 12/2003 | Markworth et al. | |
| 6,726,692 B2 | 4/2004 | Bette | |
| 6,802,852 B2 * | 10/2004 | Tontarra | 606/208 |
| 2002/0151931 A1 * | 10/2002 | Tontarra | 606/205 |
| 2003/0088268 A1 * | 5/2003 | Weinmann | 606/205 |
| 2003/0199872 A1 * | 10/2003 | Markworth et al. | 606/61 |
| 2004/0049191 A1 * | 3/2004 | Markworth et al. | 606/61 |
| 2004/0147936 A1 * | 7/2004 | Rosenberg et al. | 606/99 |
| 2004/0199170 A1 * | 10/2004 | Shluzas et al. | 606/105 |
| 2005/0033299 A1 * | 2/2005 | Shluzas | 606/61 |
| 2005/0055031 A1 * | 3/2005 | Lim | 606/99 |
| 2005/0090824 A1 * | 4/2005 | Shluzas et al. | 606/61 |
| 2005/0131419 A1 * | 6/2005 | McCord et al. | 606/99 |
| 2005/0143749 A1 * | 6/2005 | Zalenski et al. | 606/99 |

FOREIGN PATENT DOCUMENTS

SU 995769 2/1983

OTHER PUBLICATIONS

Pages 50-51, Chapter 2, The TSRH Minicorkscrew.
Cotrel-Dubousset Instrumention, one page.
Universal Spinal System Rod Introduction Pliers by Synthes Spine (13 pages).

* cited by examiner

ROD REDUCER

FIELD OF THE INVENTION

The present invention concerns tools for use in implanting orthopedic implants during surgery. Specifically, the present invention discloses a tool for reduction of a spinal support rod or other elongated orthopedic implant member.

BACKGROUND OF THE INVENTION

In orthopedic surgical procedures, it is known to implant devices to support bony or other tissue, to correct deformities, to hold tissues in position for healing after injuries or other surgery, and for other purposes relating to orthopedic health. For example, where correction of a scoliotic or other abnormal curvature of the spine is desired, a sturdy rod, plate, or other elongated implant member can be placed along one or more vertebral segments to support or hold the segments in a corrected position. Bone screws, bone hooks or other fixation implants are attached to vertebrae and connected to the elongated implant member to provide the support.

Commonly, the fixation implants and the elongated implant member(s) are placed separately, that is, they are not connected together prior to implantation in the body. For example, bone screws may be implanted into vertebrae first, connectors may be placed on or around the screws (if necessary), and then the rod may be placed into the body. The rod or other elongated implant may be contoured prior to insertion to approximate the curvature desired, or it may be contoured after placement adjacent the spine. In cases where a rod and bone screws or other fixation elements are separately placed, frequently the rod and screws must be forced toward each other for connection. The process of moving a rod or other elongated member and fixation elements toward each other for connection is generally termed "reduction" of the rod.

Reduction of a rod can be accomplished by hand, although the fluid environment of a surgical site can make reduction by hand quite difficult. Several devices have been developed to accomplish rod reduction. Among them is the device disclosed in U.S. Pat. No. 6,146,386 to Blackman et al., which is owned by the assignee of the present disclosure. That device places a cable around a fixation member and abuts a rod, so that retraction of the cable draws the fixation member and rod toward each other. Other devices have used forceps-like structures, threaded mechanisms, or other mechanical constructs to push implants together.

Most rod reducing devices are capable of use with only one or a few of the available implant systems. Accordingly, prior devices have connections that are only useful for connecting to certain fixation members or elongated members. Thus, their connections may not be useful for connecting to fixation members of another type. Further, the connections of such devices may not be used for connecting to fixation members with a smooth outside or that do not have affirmative connection points such as indentations, grooves, threads or the like.

SUMMARY OF THE INVENTION

In one embodiment, an apparatus is provided for connecting to an orthopedic implant, comprising a base having a relatively forward end and a relatively rearward end, a shaft connected to the base and slidable with respect to the base, a plate with an aperture that is pivotably connected to the shaft, and a sleeve at least partially surrounding the shaft and being slidable along the rod and with respect to the base. The shaft has a first position that corresponds to a locking position of the plate, and a second position that corresponds to an accepting position of the plate. Other embodiments of the apparatus can include a ratchet operative to move the sleeve, which can be operated by an actuator pivotably connected to a base. A stock can be attached to or integral with the base, and one or more springs can be placed between the stock and the actuator. A catch can be connected to the base, so that the catch has a first position that connects to the ratchet and inhibits movement of the sleeve in a rearward direction, and a second position disengaged from the ratchet so that the sleeve can be moved in a rearward direction.

Other aspects of this and other embodiments of apparatus and methods will be apparent from the following disclosure and the knowledge of ordinary skill in the art.

DESCRIPTION OF THE PREFERRED EMBODIMENTS

Figure 1:
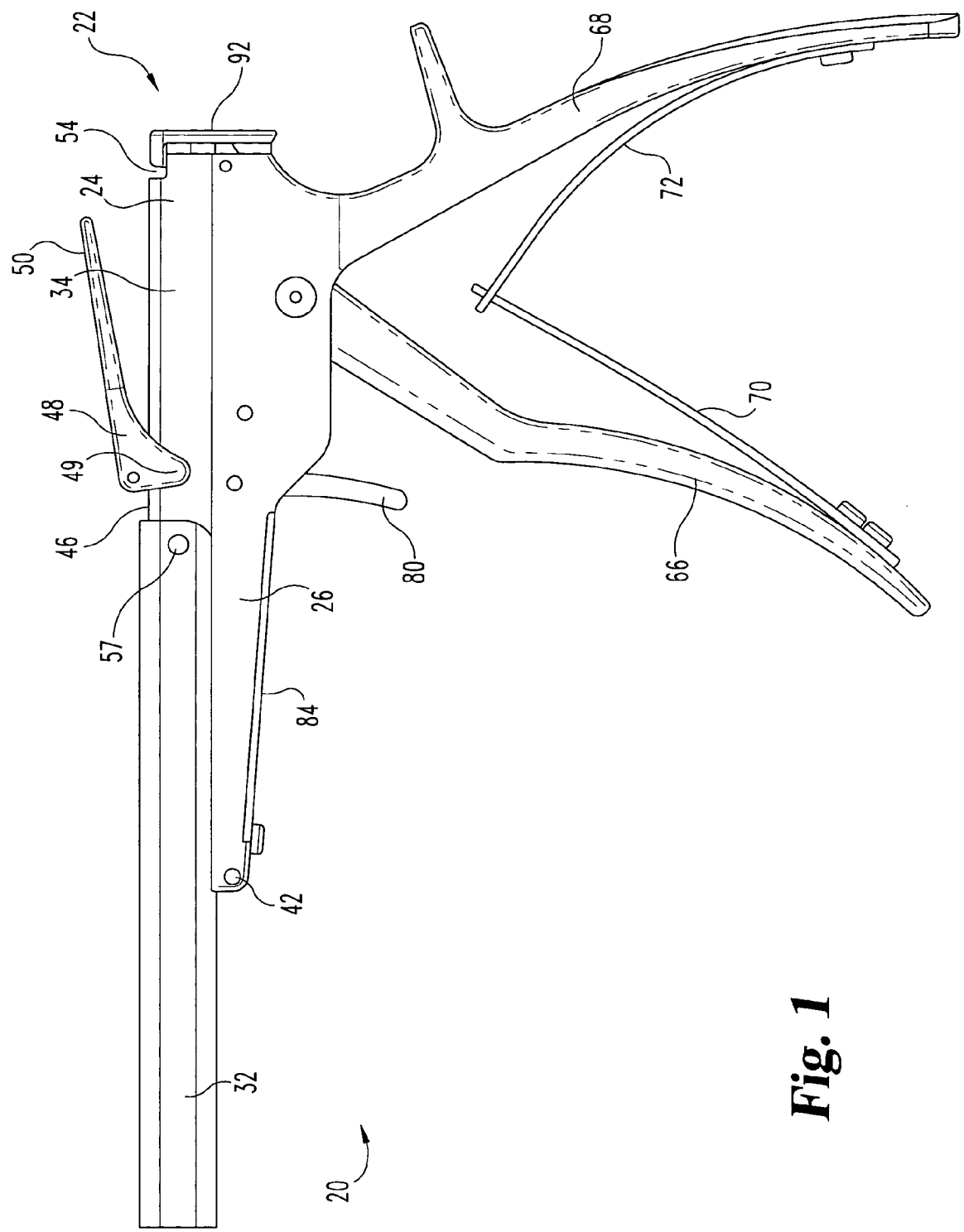
FIG. 1 is a side view of one embodiment of a rod reducer incorporating aspects of the present invention.
Figure 2:
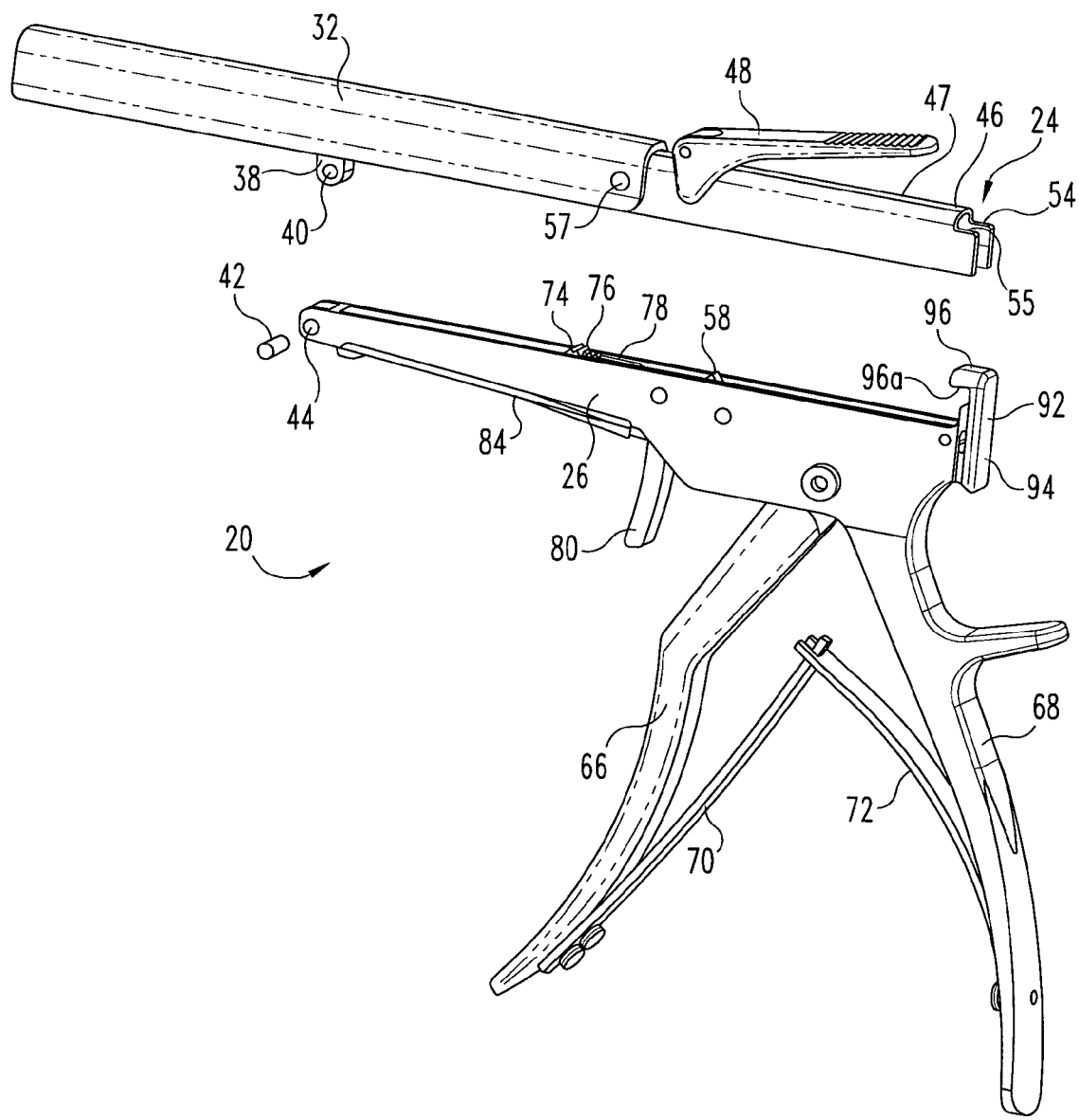
FIG. 2 is a perspective exploded view of the embodiment shown in FIG. 1.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates are also included.

Referring now generally to FIGS. 1-12, there is shown one embodiment of a rod reducer 20. In that embodiment, rod reducer 20 includes a base 22 (including an upper base portion 24 and a lower base portion 26 in the illustrated embodiment), a shaft element 28, a plate element 30, and a sleeve element 32. Shaft element 28 is slidable with respect to base 22. Plate element 30 is pivotably connected to shaft 28 at or near an end of shaft 28. Sleeve 32 is slidably coupled to base 22 independently of shaft 28.

Base 22 in the illustrated embodiment includes upper base portion 24 and lower base portion 26. Upper base portion 24 is roughly rectangular, having a relatively rearward part 34 and a relatively forward part 36. Upper base portion 24 is pivotally connected to lower base portion 26, as by a flange 38 with a hole 40 that extends into lower base portion 26 and is connected thereto by a pin 42 extending through hole 40 and a hole 44 in lower base portion 26. In that embodiment, the base portions 24 and 26 are relatively pivotable about pin 42.

Upper portion 24 and/or lower portion 26 of base 22 may be hollow through much or all of their respective extents. In one embodiment of upper base portion 24, an upper surface 46 includes an opening 47 through which shaft element 28 can be contacted by a button or lever, such as lever 48, as will be described further below. Lever 48 is pivotally connected to upper base portion 24 at an end portion 49, so that pressing on a part of pad 50 will pivot lever 48 about end portion 49. Upper portion 24 also includes in the illustrated embodiment a slot 51 in a side surface, and may include a second slot similar or identical to slot 51 in the opposite side surface. Upper portion 24 may include an end portion 52 having a cavity 53 formed therein. Cavity 53 may be generally cylindrical or rectangular, and may have an extension portion 53a at a proximal end. In an embodiment in which rod reducer 20 includes a closure (described below), upper base portion 24 can include a notch 54. Notch 54 may have a surface 55 that is slanted, i.e. substantially non-parallel to the remainder of upper base portion 24, to enhance the connection and lock of the closure.

A toothed bar 56 sits substantially within upper base portion 24, and is able to slide within base 22 (one or both of base portions 24 and 26) between a forward and rearward position. Bar 56 is attached through slot(s) 51 in upper base portion 24 to sleeve 32, so that movement of bar 56 causes substantially identical movement of sleeve 32. In the illustrated embodiment, a connecting pin 57 connects bar 56 to sleeve 32 through slot 51. It will be seen that in place of a pin, a rivet, a weld, or other structure for connecting bar 56 and sleeve 32 can be used.

Lower base portion 26 includes a ratchet mechanism for moving sleeve 32 with respect to base 22, shaft 28 and plate 30. The mechanism includes a drive pawl 58 having a tooth 60 configured to engage toothed bar 56 and a slot 62, which sits substantially within lower base portion 26. Slot 62, in one embodiment, has a slanted portion 62a, and accommodates a pin or boss 63 connected to lower base portion 26. The mechanism may also include a spring 64 (shown with cap 65) to bias pawl 58. Pawl 58 is pivotably connected at a point adjacent one end to an actuator arm 66. Actuator arm 66 is in turn pivotably connected at a point adjacent one end to lower base portion 26. In this embodiment, lower base portion 26 may also be provided with a stock or stationary arm 68, which is integral with or attached to lower base portion 26. One or more springs may also be provided to bias actuator arm 66 away from base portion 26 or stock 68. In the illustrated embodiment, two leaf springs 70 and 72 are provided. Spring 70 is attached to actuator arm 66, spring 72 is attached to stock 68, and springs 70 and 72 are connected to each other. It will be understood that a single leaf spring, for example spring 70, may be provided to bias arms 66 and 68 apart. Other structures, such as one or more coil springs or other springs, can be used in addition to or instead of leaf springs 70 and/or 72 to provide such bias.

Squeezing actuator arm 66 toward stock 68 causes pawl 58 to move relatively forward, and in doing so spring 64 pushes pawl upward until tooth 60 engages bar 56. Pawl 58 thus moves bar 56 relatively forward. When actuator arm 66 is released and is biased back to a position spread from stock 68, pawl 58 moves relatively backward, and when slanted portion 62a of slot 62 contacts pin 63, pawl 58 is forced downward and compresses spring 64.

At least one pawl for preventing or inhibiting retrograde movement of bar 56 (and sleeve 32) is also provided in the illustrated embodiment. Although only a single pawl can be used with rod reducer 20, in the illustrated embodiment a three-pawl mechanism is provided. Pawl 74 has one tooth 74a, and a slot 74b. Pawl 76 has two teeth 76a, a pin 76b that extends at least partially through slot 74b, and a slot (not shown) similar to slot 74b. Pawl 78 has three teeth 78a in this embodiment and may have a pin 78b that cooperates with the slot of pawl 76. In this embodiment, pawls 74, 76, 78 are nested, e.g. pawls 74 and 76 are substantially hollow, and pawl 78 fits at least partially within the hollow of pawl 76, and pawls 76 and 78 fit at least partially within pawl 74. Pawl 74 may be connected to or integral with a release lever 80, which is pivotally connected to lower base portion 26 as at point 82. Pulling release lever 80 pivots pawl 74. Pawl 74 may move with respect to pawls 76 and/or 78, at least until an end of slot 74b contacts pin 76b, at which time further pulling of lever 80 pivots pawl 76 as well. A similar relationship can exist between pawl 76 (and its slot) and pawl 78 and its pin 78b. The teeth of adjacent pawls (e.g. pawls 74 and 76, or pawls 76 and 78) may be spaced apart a specific amount that is smaller than and/or not an integer-multiple of the distance between the teeth (crest to crest or trough to trough) of the toothed bar 56, so that incremental advancements of bar 56 (and sleeve element 32) can be made that are smaller than the distance between the teeth of bar 56. For example, reducer 20 may include a bar 56 having a space of two millimeters (2 mm) between teeth. A pawl having multiple teeth (i.e. pawls 76 and 78 in the illustrated embodiment) will also have two millimeters between the teeth to mate properly with bar 56. However, the distance between the pawls may be set at 0.7 millimeters, in a specific embodiment. Thus, starting from a position in which one pawl is engaged with bar 56 (i.e. crest(s) on the pawl in associated trough(s) of bar 56), a 0.7 millimeter advancement of bar 56 will result in the teeth of another pawl engaging bar 56.

A leaf spring 84 is provided in this embodiment, connected to the underside of lower base portion 26. Spring 84 can include three substantially parallel fingers 86, 88, 90, each of which tends to bias one of the pawls 74, 76, 78. Thus, finger 86 of spring 84 biases pawl 74 upward and into contact with bar 56, finger 88 similarly biases pawl 76 upward, and finger 90 similarly biases pawl 78 upward.

The illustrated embodiments of upper base portion 24 and lower base portion 26 also include a closure that locks together base portions 24 and 26 during use, and can be opened to allow upper base portion to be pivoted away from lower base portion 26. Opening reducer 20 in this fashion allows cleaning, sterilization, maintenance or other operations to be performed on the apparatus within base 22, including the above-described ratchet mechanism, pawls, release lever, toothed bar, or other features. In one embodiment, a latch 92 having an end plate 94 and a top flange 96 is pivotably connected to a substantially C-shaped connector 98, which in turn is pivotably connected to lower base portion 26. Flange 96 may be complementary with notch 54 of upper base portion 24. For example, the length of flange 96 may be substantially the same as the length of notch 54, and flange 96 may have an underside 96a that has the same angle as slanted surface 55. Latch 92 may be released by lifting its lower end so that connector 98 pivots with respect to lower base portion 26 and latch 92 and lifts flange 96 away from notch 54, and by pivoting latch 92 away from upper base portion 24. Latch 92 may be engaged in substantially the reverse manner, by positioning flange 96 adjacent to notch 54 then pressing down on latch 92 until latch 92 and connector 98 pivot and snap into place, with end plate 94 abutting upper end portion 24 and lower end portion 26.

Shaft element 28 may be elongated and roughly rectangular. In the illustrated embodiment, shaft 28 extends adjacent top surface 46 of upper base portion 24, to a point adjacent to or at the end of relatively forward part 34 of base 22. In one embodiment a relatively rearward portion or end of shaft 28 is attached to a lever 48 through opening 47 in relatively rearward part 34 of upper base portion 24. As previously described, lever 48 can be pivoted by the user so as to move shaft 28 along upper base portion 24.

In a specific embodiment, shaft 28 has an elongated portion 100 and a plunger 102 connected to a relatively forward part of elongated portion 100. Elongated portion 100 is connected to lever 48 at or near one end, and includes a tab or tongue 104 that connects to plunger 102 and an indentation 106 for connecting with plate member 30, as will be described further below. Plunger 102 includes a groove 108 that accommodates tongue 104 and a rear portion 110 having an end surface 112 and a ledge 114. Alternatively, plunger 102 and elongated portion 100 could be integral or otherwise connected or attached.

The illustrated embodiment includes an inner coil spring 116 and an outer coil spring 118 for biasing shaft 28 forward. Spring 116 abuts end surface 112, and spring 118 abuts ledge portion 114 of plunger 102. Both springs abut an end surface of cavity 53 in upper base portion 24, and if extension portion 53a of cavity 53 is present, inner spring 116 may extend within extension portion 53a. Springs 116 and 118 may be concentric. Other types of biasing devices could be used in place of one or both coil springs 116 and 118, or only one spring could be used, to bias plunger 102 and shaft 28 forward. When lever 48 is depressed, it pivots to move shaft 28 relatively backward, and springs 116 and 118 are compressed between plunger 102 and a surface of cavity 53. When lever 48 is released, springs 116 and 118 force plunger 102 and shaft 28 forward. A block element 119 or other barrier may be provided to limit the forward range of motion of plunger 102

Plate element 30, in the illustrated embodiment, is a substantially rectangular piece with an aperture 120 and an upper notch or gap 122. Aperture 120 can go all the way through plate 30, or may end within plate 30. Gap 122 is sized to accommodate a portion of shaft 28. As one example, notch 122 can accommodate a part of elongated portion 100 of shaft 28. Plate element 30 has an upper edge 124, a rounded surface 126 adjacent upper edge 124 and gap 122, and a lower rounded edge 128. Rounded surfaces 126 and 128 facilitate pivoting of plate 30. In one embodiment, indentation 106 of shaft element 28 may fit with rounded surface 126, so that indentation 106 and rounded surface 126 are able to rotate with respect to each other. Thus, linear movement of shaft 28 causes indentation 106 to move linearly and push plate element 30, so that indentation 106 and rounded surface 126 move with respect to each other and plate 30 pivots substantially around rounded edge 128. Alternatively, plate element 30 could be connected to shaft element 28 in or adjacent to gap 122 by placing a pin or axle through shaft 28 and connecting to plate 30 on either side of gap 122, so that plate 30 can pivot with respect to shaft 28. As another example, plate 30 could include extensions in or adjacent to gap 122 that may be inserted into shaft 28 and act as an axle for plate 30.

In one specific embodiment, aperture 120 of plate element 30 is partially tapered. For example, aperture 120 can include a constant-diameter portion 130 and a varying-diameter portion 132. Alternatively, aperture 120 may have a constant diameter throughout, may be uniformly tapered throughout, or may have other surface configurations. The minimum diameter of aperture 120 is at least somewhat larger than the external diameter or other dimension of a bone fixation member with which reducer 20 is to be used. Further, in a specific embodiment tapered portion 132 is oriented so that the largest diameter of tapered portion 132 is on the distal surface of plate 30, i.e. that surface furthest from lever 48, to make insertion of a part of a bone fixation member into aperture 120 (as described below) easier. Plate element 30 and its aperture 120 form a locking mechanism for holding a fixation member within rod reducer 20. The surfaces of plate element 30, including those bounding aperture 120, could be roughened as with knurling, one or more grooves or ridges, or with other surface irregularities or roughening methods in addition to or in place of a tapered configuration. Such roughening can create or improve contact, grip or purchase between plate 30 and a fixation member during use of rod reducer 20.

Figure 3:
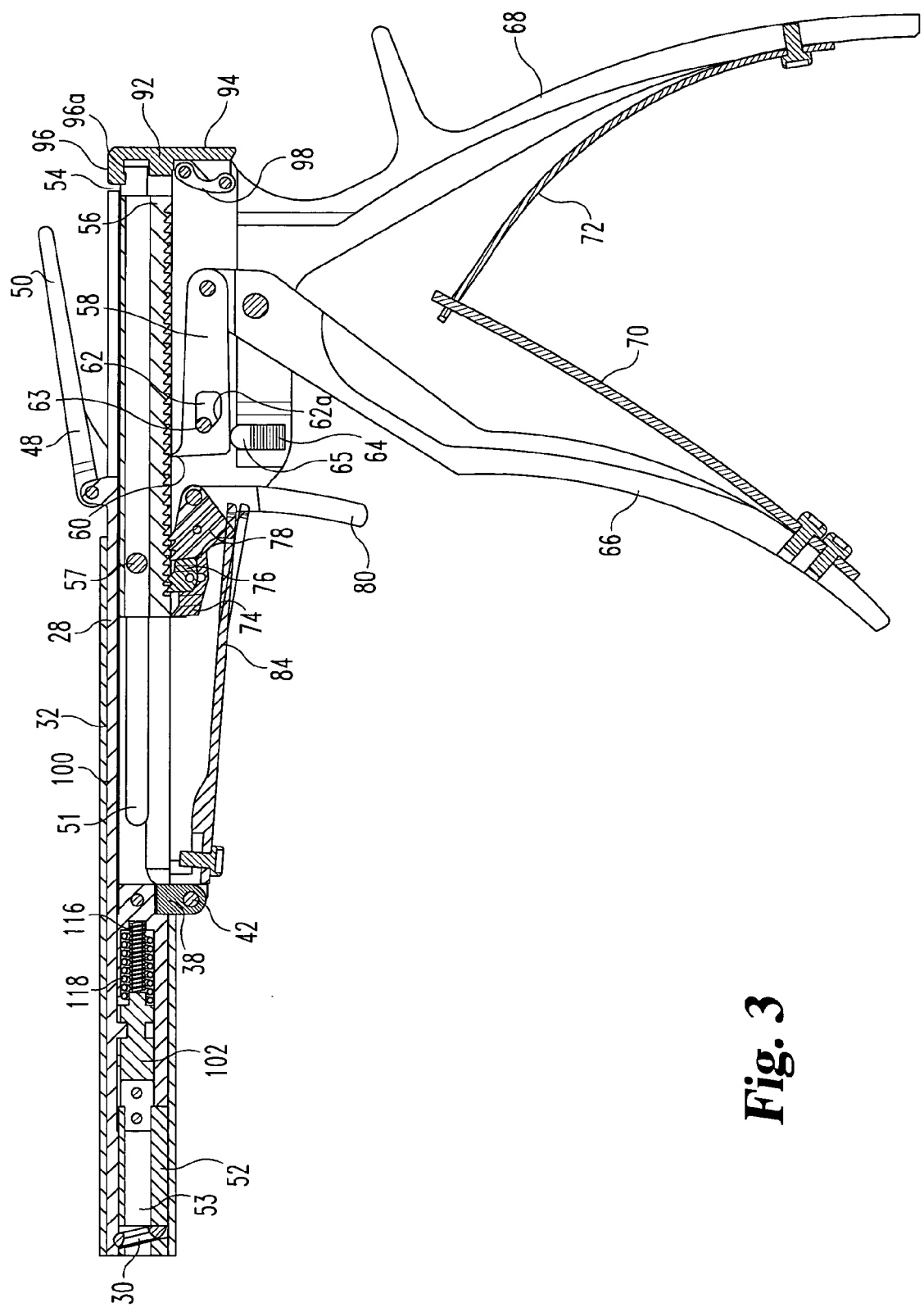
FIG. 3 is a sectional view from the side of the embodiment shown in FIG. 1.
Figure 4:
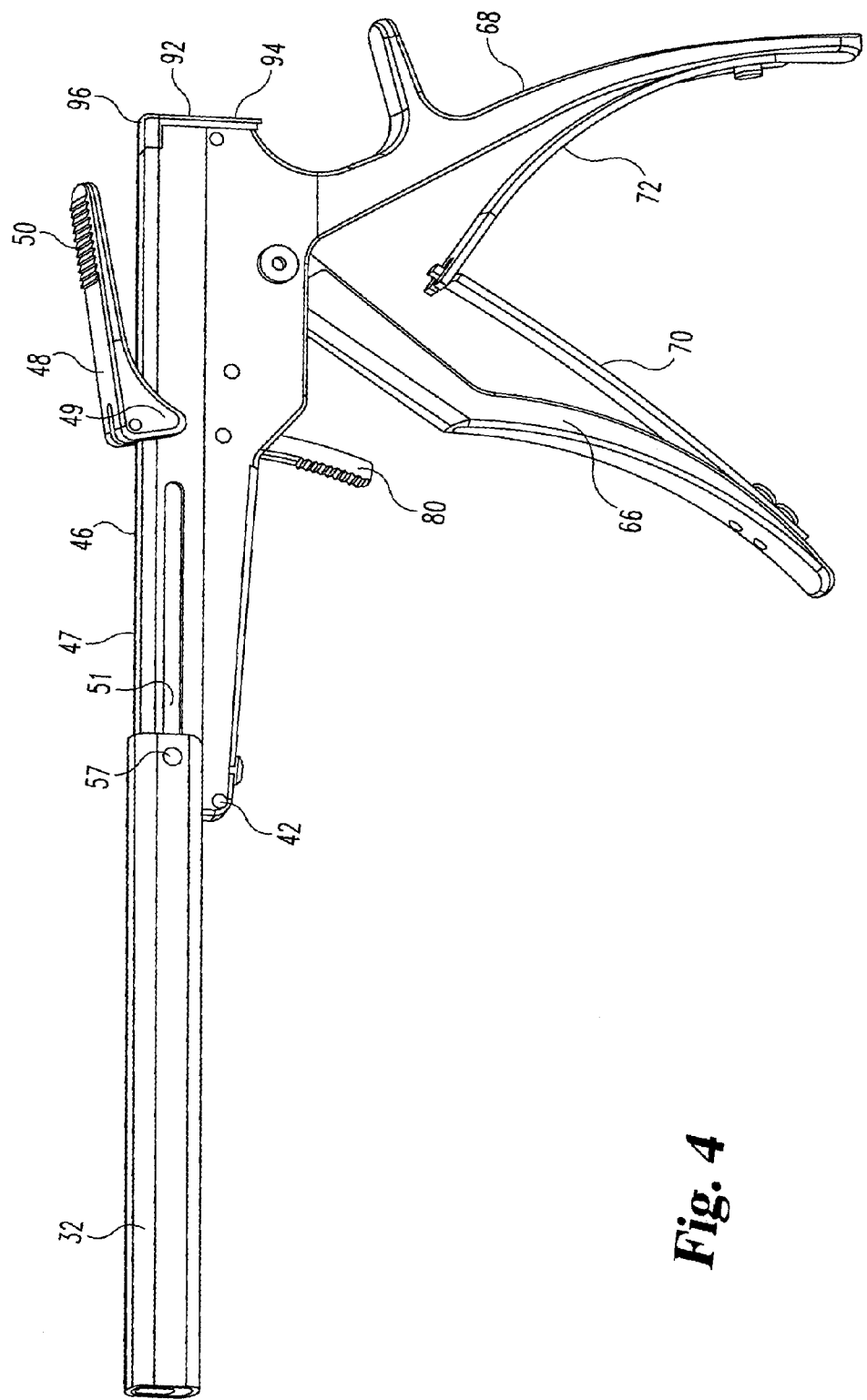
FIG. 4 is a perspective view of the embodiment shown in FIG. 1 in an extended state.
Figure 5:
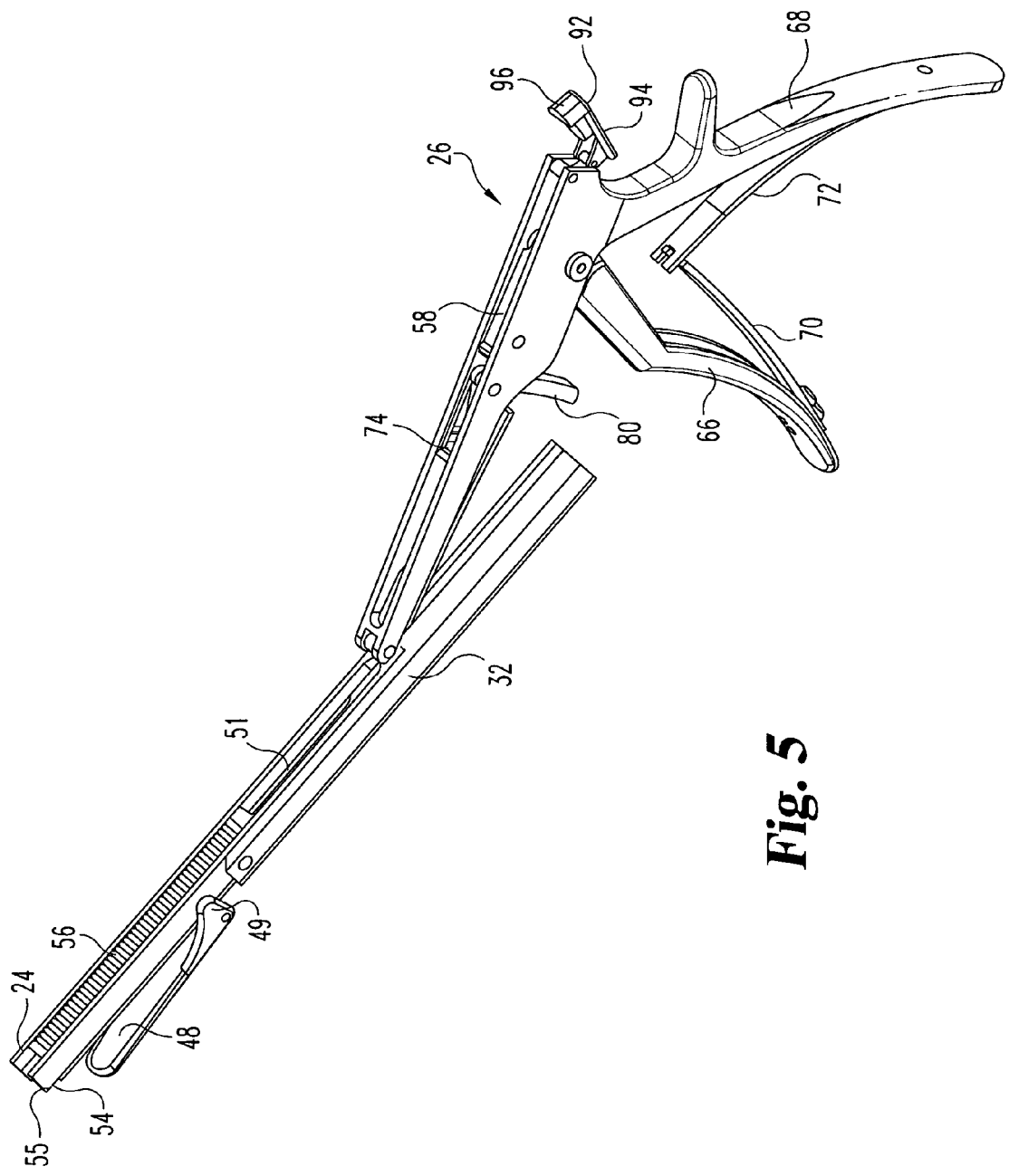
FIG. 5 is a perspective view of the embodiment shown in FIG. 1 in an open state.
Figure 6:
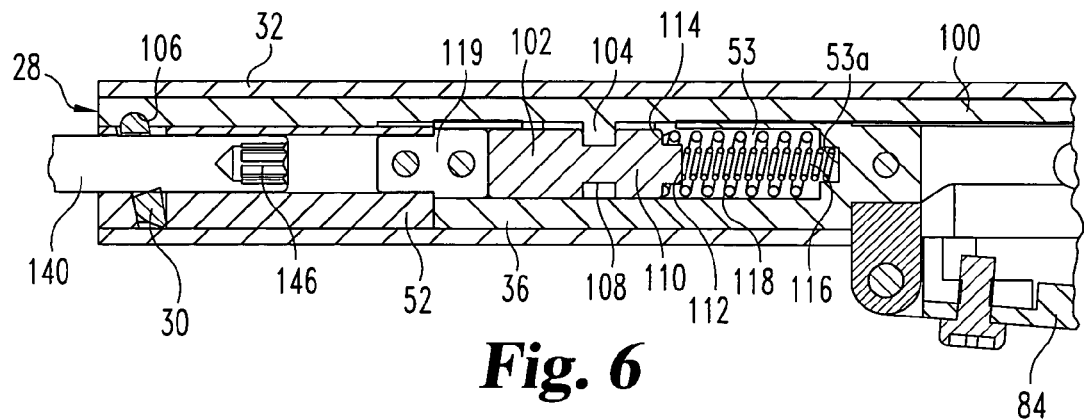
FIG. 6 is a sectional view from the side of a forward part of the embodiment shown in FIG. 1 with a fixation element in a relatively gripped state.
Figure 7:
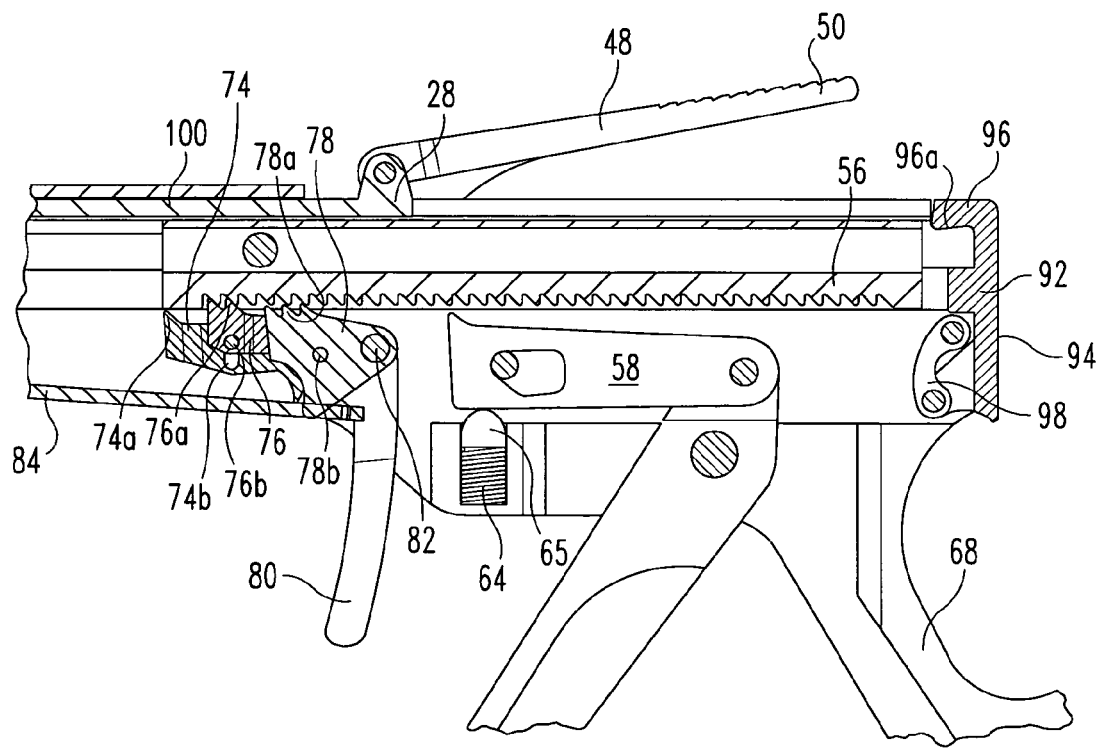
FIG. 7 is a sectional view from the side of a rearward part of the embodiment shown in FIG. 1.
Figure 8:
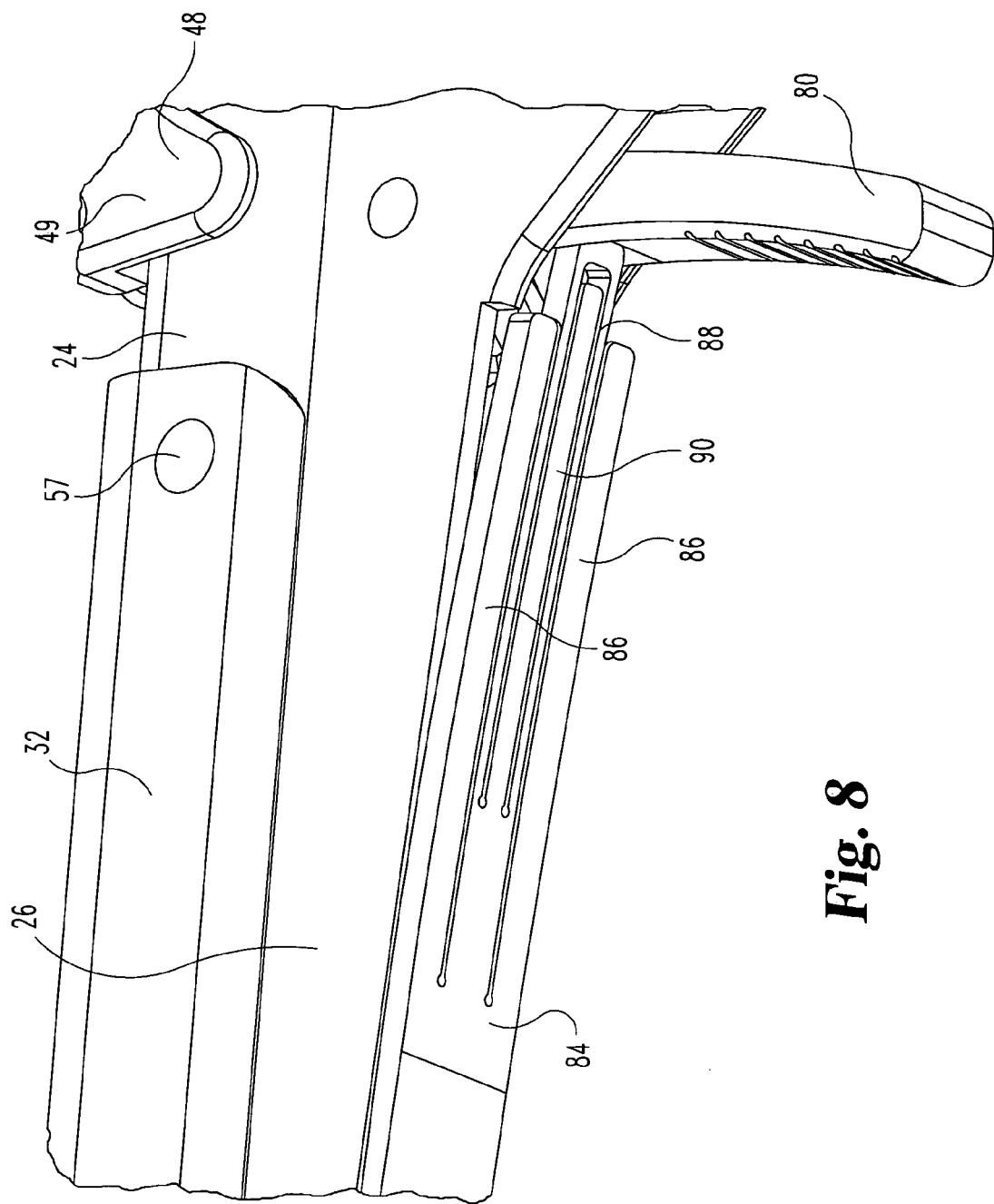
FIG. 8 is a perspective view of a lower portion of the embodiment shown in FIG. 1.
Figure 9:
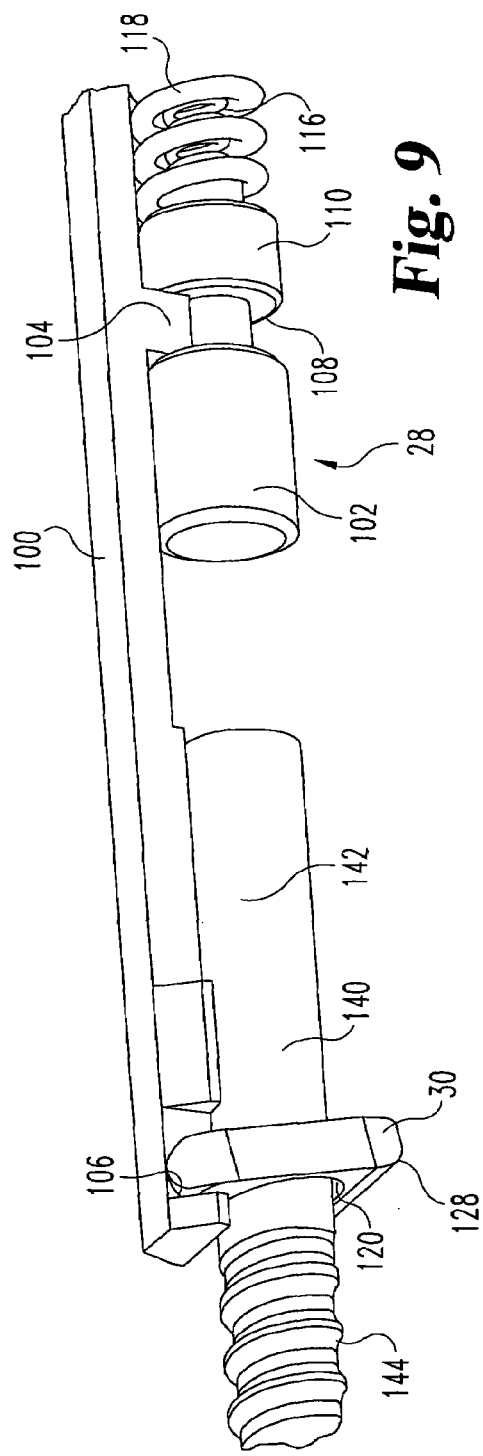
FIG. 9 is a perspective view of an embodiment of a portion of a shaft element and connected structure, in a relatively gripping state, used in the embodiment shown in FIG. 1.
Figure 10:
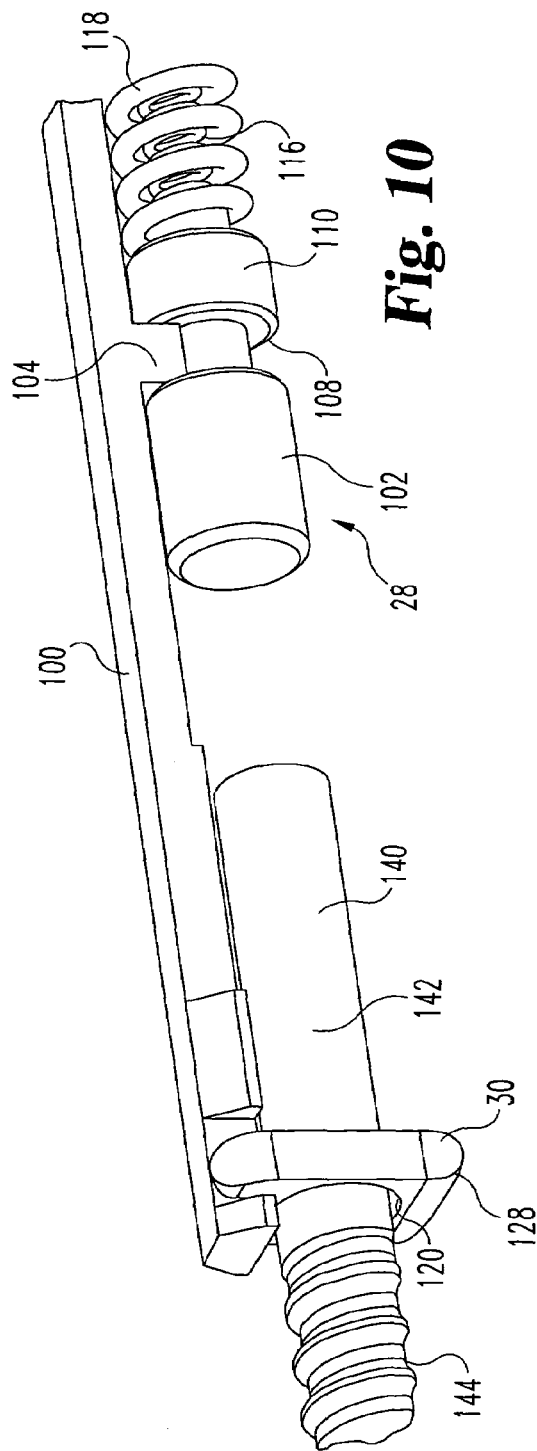
FIG. 10 is a perspective view of the embodiment shown in FIG. 9 in a relatively open or inserting state.
Figure 12:
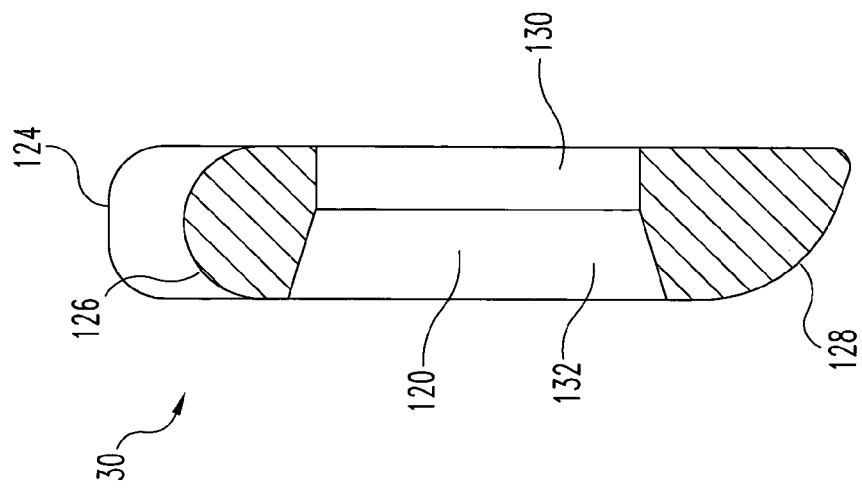
FIG. 12 is a sectional view, taken along the lines 12-12 in FIG. 11, of the embodiment of the plate member shown in FIG. 11.
Figure 11:
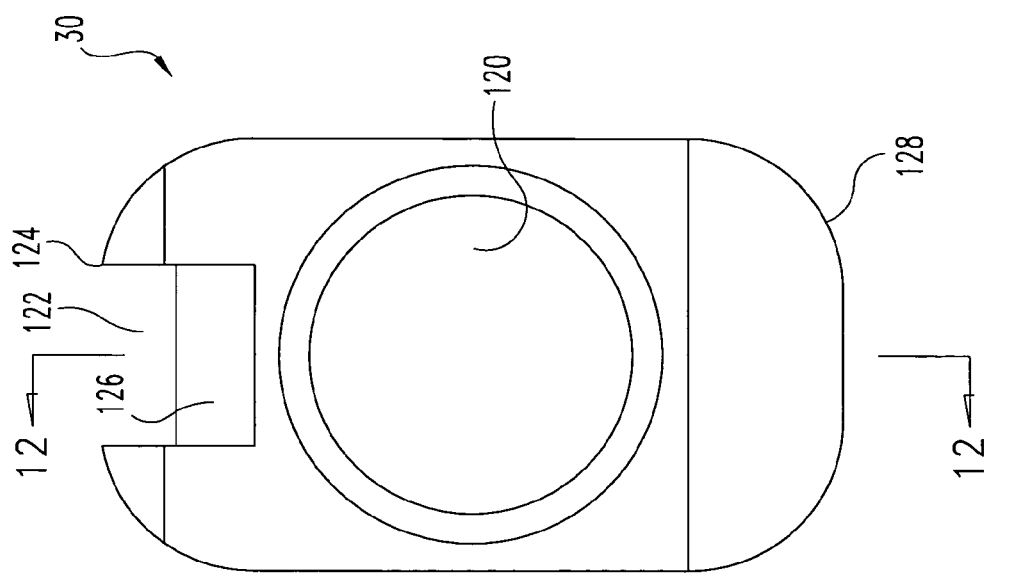
FIG. 11 is a front view of an embodiment of a plate member used in the embodiment shown in FIG. 1.

Sleeve element 32 is a generally hollow rectangular member in the illustrated embodiment, though other configurations could also be used. Sleeve 32, as noted above, is slidably connected to base 22, particularly upper base member 24, between a relatively rearward position and a relatively forward position. One example of a relatively rearward position of sleeve element 32 is shown in FIGS. 1 and 3, where sleeve 32 covers a substantial portion of upper base portion 24, and one end of sleeve 32 is adjacent lever 48 while the other end of sleeve 32 is adjacent a distal end of shaft element 28 and plate element 30. An example of a relatively forward position is shown in FIG. 4, where sleeve 32 covers a lesser portion of upper base portion 24, and a distal end of sleeve 32 extends substantially beyond the distal end of shaft element 28. In a specific embodiment, sleeve 32 can have a range of sliding movement of about fifty millimeters, i.e., the distal end of sleeve 32 is about fifty millimeters further from base 22 when sleeve 32 is in a relatively forward-most position than when sleeve 32 is in a relatively rearward-most position. Sleeve 32 is also slidable relative to shaft element 28 and plate element 30. Sleeve element 32 may have a distal portion or end that is substantially flat, or may be otherwise configured, and may be intended for contact with implants such as a spinal rod, an orthopedic connector, and/or an orthopedic plate The use of rod reducer 20 will now be described in the context of use with a substantially cylindrical bone screw 140 (FIG. 6, 9-10), such as a Schanz-type screw, and a rod for spinal correction. The illustrated embodiment of screw 140 has a substantially cylindrical upper part 142 and a threaded lower part 144. The upper part 142 may have an external or internal print to enable screw 140 to be threaded into a bone or otherwise manipulated. Screw 140 may have a print 146, which may be hexagonal and internal as shown or may be of other configuration (e.g. hexalobed or slotted internal print, or an external hexagonal or square print). The threads of threaded part 144 are intended to be securely fastened into a bone, and may be cancellous threads or another variety of threads useful in orthopedic surgery. Such screws may be used in or among one or more parts of the spine, including cervical, thoracic, lumbar and/or sacral portions. Although the use of rod reducer 20 will be described in the above context, rod reducer 20 could be used with a variety of screws, hooks or other fixation implants, with an elongated implant member other than a rod, or in connection with orthopedic implants in other parts of the body than the spine.

As with other types of orthopedic surgery, an incision is made and access is gained to the surgical site. The approach to the surgical site can be an open approach, i.e. a relatively long incision with retraction of underlying tissue, or can be a minimally-invasive approach, i.e. a relatively short incision with implants and tools inserted through tubes or other devices to the surgical site. The embodiments disclosed herein can be used in either approach, or with other surgical techniques. It is noted that a relatively narrow distal end of rod reducer 20 will be advantageous in minimally-invasive surgery.

After access to the surgical site has been obtained, screws such as screw 140 are inserted into bone tissue. Such screws may be pre-fitted with connectors (not shown), which commonly have an aperture for receiving a part of a screw 140 and a channel for accommodating part of an elongated support member. Such connectors may be placed on or over such screws after insertion of screws 140 into bone. An elongated member, such as a spinal or other orthopedic rod, is inserted into the surgical site, and placed adjacent one or more of screws 140. If not already present, connectors may be loosely placed on the rod prior to insertion of the rod to the surgical site. In that case, the rod is inserted, and the connectors can be moved with respect to the rod until each is on or over a screw 140. The screws, connectors and rod are manipulated so that a part of the rod is in or near the channel of each connector, and each screw 140 extends through the aperture of a connector so that a portion of the screw 140 sticks out of the connector.

Rod reducer 20 is inserted to the surgical site. The surgeon or other operator moves shaft 28 backward to a relatively backward position, in one embodiment by pressing lever 48. Pressing lever 48 moves shaft element 28 backward, as described above, and causes plate element 30 to pivot. In a specific embodiment, plate 30 pivots to a position substantially perpendicular to sleeve element 32, and/or to a position such that aperture 120 of plate 30 is substantially perpendicular to sleeve 32. A portion of the upper part 142 of screw 140 is inserted into aperture 120.

Once a portion of screw 140 is within aperture 120, the surgeon moves shaft element 28 forward to a relatively forward position. In one embodiment, the surgeon may simply release lever 48, allowing springs 116, 118 to bias shaft 28 to a forward position. When shaft 28 moves to a relatively forward position, plate 30 pivots so that the surface bounding tapered portion 132 of aperture 120 (and/or the surface bounding constant-diameter portion 130) contacts a part of screw 140. In embodiments in which such surface is knurled or otherwise roughened, and/or springs 116, 118 is relatively strong, parts of plate 30 may bite into or otherwise deform a part of screw 140, or part(s) of plate 30 may be deformed. With shaft 28 in a relatively forward position, screw 140 is held by plate 30.

With screw 140 so gripped, the surgeon abuts the distal end of sleeve 32 against the rod or other implant, device or tissue. The surgeon squeezes actuator arm 66 toward stock 68, causing toothed bar 56 and sleeve 32 to move distally or away from lever 48 on upper base portion 24, as discussed above. Sleeve 32 slides around upper base portion 24, plate 30 and screw 140. Consequently, when actuator arm 66 is squeezed, sleeve 32 is forced against the implant or other structure it abuts. Such implant or structure moves with respect to screw 140 and the tissue to which it is connected, such that screw 110 moves closer to or past such implant or other structure.

For example, where a spinal rod is being reduced into a connector piece connected to screw 140, sleeve 32 abuts the rod. When actuator arm 66 is squeezed, sleeve 32 pushes the rod toward or past screw 140, and the rod can be pushed or otherwise maneuvered in this way into an opening in the connector piece connected to screw 140. Similarly, if a connector or other implant part must be pushed further onto a fixation member such as screw 140, sleeve 32 is placed so that it abuts such implant and screw 140 is connected to plate 30, then actuator arm 66 is squeezed one or more times until the desired relative position of fixation member and implant is achieved.

Bar 56 and sleeve 32 are retained in position by one or more of pawls 74, 76, 78 when actuator arm 66 is released by the surgeon between squeezes or after the desired amount of movement of sleeve 32 is achieved. Actuator arm 66 is squeezed one or more times until sleeve 32 pushes the implant or other structure it abuts a desired distance with respect to screw 140. When that desired distance is reached, for example when a spinal rod is reduced so that it sits at least partially within another implant part, then the surgeon can secure the rod to the other implant part or take other fixation or surgical action.

When reduction is no longer needed, the surgeon can press lever 48, causing shaft 28 to move rearward and pivot plate 30. In a specific embodiment, plate 30 pivots to a position substantially perpendicular to sleeve element 32, and/or to a position such that aperture 120 of plate 30 is substantially perpendicular to sleeve 32. Screw 140 can be disengaged and withdrawn from plate 30. Catch 96 can be pulled to reset bar 56 and sleeve 32 to a relatively rearward position, and allow reducer 20 to be used with respect to other screws or implants in the given patient. Reducer 20 can be made for use with a single patient, or as noted above may be made to be cleaned and sterilized for later use with other patients, as for example by releasing latch 92 and pivoting upper base portion 24 with respect to lower base portion 26 for access to internal parts of reducer 20.

It will be seen that several changes may be made to the above structure. For example, shaft 24 may be made of a single piece, rather than several interconnected pieces. Spring 68 is preferably a coiled compression spring, but an extension spring or other types of springs may be used in addition to or in place of spring 68. Reducer 20, or parts of it, are preferably made of biocompatible materials such as stainless steel or certain sturdy plastics. The materials for making reducer 20 may also be chosen to allow resterilization and reuse of reducer 20.

Other embodiments of rod reducer 20 or parts of it are also possible. For example, a rod reducer 20 in which upper base portion 24 and lower base portion 26 are fixed together or integral with each other so that those portions are not separable or pivotable with respect to each other. Base 22 may be effectively a single piece, housing or connected to the structures described above.

In place of lever 48, a button or slider could be connected to shaft 28 to enable the user to pull back on shaft 28. Such a slider may be substantially triangular, concave, or otherwise configured, and may be situated atop upper surface 46. Pulling back on the slider retracts shaft 28 to rotate plate 30 and allow a fixation member to be inserted through plate 30. Releasing the slider allows shaft 28 to be biased forward to rotate plate 30 to lock onto or hold the fixation member.

In other embodiments, a single spring may be used to bias plunger 102 relatively forward. Plunger 102 and the forward part of base 22 could be configured to use an extension spring for such bias. In that case, pulling back on shaft 28 would extend such a spring, and releasing shaft 28 would allow such a spring to pull plunger 102 and the rest of shaft 28 forward. If desired, plunger 102 can be made of two or more connected parts. Further, plate member 30 may be of a somewhat different configuration. For example, plate 30 could be substantially square or of other shape.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus for connecting to an orthopedic implant, comprising:
    a base having a relatively forward end and a relatively rearward end;
    a shaft connected to said base, said shaft being slidable with respect to said base between first and second positions;
    a plate having an aperture, said plate being pivotably connected to said shaft, such that when said shaft is in said first position said plate is in a position for locking to an implant, and when said shaft is slid to said second position, said plate pivots to a position for accepting insertion of a part of an implant;
    a sleeve at least partially surrounding said shaft and being slidable along said shaft and slidable with respect to said base and said plate;
    a ratchet mechanism connected to said base and said sleeve, said ratchet mechanism operable to move said sleeve with respect to said base, said shaft and said plate; and
    a handle including an actuator movably connected to said base, said actuator operating said ratchet mechanism when said actuator is moved relative to said base.

2. The apparatus of claim 1, wherein said actuator is pivotably connected to said base, said actuator operating said ratchet mechanism when said actuator is pivoted relative to said base.

3. The apparatus of claim 2, wherein said handle further includes a stock rigidly connected to said base.

4. The apparatus of claim 3, further comprising at least one spring between said actuator and said stock, said at least one spring tending to bias the actuator and stock apart.

5. The apparatus of claim 4, wherein said at least one spring comprises a leaf spring.

6. The apparatus of claim 4, wherein said at least one spring comprises a first leaf spring connected to said actuator and a second leaf spring connected to said stock, wherein said leaf springs are connected together so as to bias the actuator and stock apart.

7. The apparatus of claim 4, further comprising a stop connected to said base, said stop having a first position connected to said ratchet mechanism so that movement in a rearward direction of said sleeve is limited, and a second position disengaged from said ratchet mechanism so that said sleeve can be moved in a rearward direction.

8. The apparatus of claim 7, wherein said stop is biased toward said first position.

9. An apparatus for connecting to an orthopedic implant, comprising:
    a base having a relatively forward end and a relatively rearward end;
    a shaft connected to said base, said shaft being slidable with respect to said base between first and second positions;
    a plate having an aperture, said plate being pivotably connected to said shaft, such that when said shaft is in said first position said plate is in a position for locking to an implant, and when said shaft is slid to said second position, said plate pivots to a position for accepting insertion of a part of an implant;
    a sleeve at least partially surrounding said shaft and being slidable along said shaft and slidable with respect to said base and said plate;
    a ratchet mechanism connected to said base and said sleeve, said ratchet mechanism operable to move said sleeve with respect to said base, said shaft and said plate; and
    a stop connected to said base, said stop having at least one position connected to said ratchet mechanism in which movement in a rearward direction of said sleeve is limited, and a position disengaged from said ratchet mechanism so that said sleeve can be moved in a rearward direction.

10. The apparatus of claim 9, wherein said stop comprises at least one pawl that is pivotable between said at least one position connected to said ratchet mechanism and said position disengaged from said ratchet mechanism.

11. The apparatus of claim 10 wherein said stop comprises three pawls capable of operating independently of each other.

12. The apparatus of claim 11 wherein said pawls are nested.

13. An apparatus for connecting to an orthopedic implant, comprising:
    a base having a relatively forward end and a relatively rearward end;
    a shaft connected to said base, said shaft being slidable with respect to said base between first and second positions;
    a plate having an aperture, said plate being pivotably connected to said shaft, such that when said shaft is in said first position said plate is in a position for locking to an implant, and when said shaft is slid to said second position, said plate pivots to a position for accepting insertion of a part of an implant; and
    a sleeve at least partially surrounding said shaft and being slidable along said shaft and slidable with respect to said base and said plate,
    wherein said aperture of said plate is at least partially tapered.

14. The apparatus of claim 13, wherein said aperture of said plate has a constant diameter section.

15. The apparatus of claim 13, wherein said plate includes a roughened surface adjacent said aperture.

16. The apparatus of claim 13, wherein said aperture of said plate is uniformly tapered.

17. An apparatus for connecting to an orthopedic implant, comprising:
    a base having a relatively forward end and a relatively rearward end;
    a shaft connected to said base, said shaft being slidable with respect to said base between first and second positions;
    a plate having an aperture, said plate being pivotably connected to said shaft, such that when said shaft is in said first position said plate is in a position for locking to an implant, and when said shaft is slid to said second position, said plate pivots to a position for accepting insertion of a part of an implant;

a sleeve at least partially surrounding said shaft and being slidable along said shaft and slidable with respect to said base and said plate; and wherein said plate includes a rounded surface and said shaft includes an indentation, and said indentation and said rounded surface are adjacent each other.

18. An apparatus for connecting to an orthopedic implant, comprising:
a base having a relatively forward end and a relatively rearward end;
a shaft connected to said base, said shaft being slidable with respect to said base between first and second positions;
a plate having an aperture, said plate being pivotably connected to said shaft, such that when said shaft is in said first position said plate is in a position for locking to an implant, and when said shaft is slid to said second position, said plate pivots to a position for accepting insertion of a part of an implant;
a sleeve at least partially surrounding said shaft and being slidable along said shaft and slidable with respect to said base and said plate; and
wherein said plate includes a rounded surface that facilitates pivoting of said plate.

19. An apparatus for connecting to an orthopedic implant, comprising:
a base having a relatively forward end and a relatively rearward end;
a shaft connected to said base, said shaft being slidable with respect to said base between first and second positions;
a plate having an aperture, said plate being pivotably connected to said shaft, such that when said shaft is in said first position said plate is in a position for locking to an implant, and when said shaft is slid to said second position, said plate pivots to a position for accepting insertion of a part of an implant;
a sleeve at least partially surrounding said shaft and being slidable along said shaft and slidable with respect to said base and said plate; and
wherein said sleeve includes an end portion adapted to contact at least one of the group consisting of a spinal rod, an orthopedic connector, and an orthopedic plate.

20. An apparatus for connecting to an orthopedic implant, comprising:
a base having a relatively forward end and a relatively rearward end;
a shaft connected to said base, said shaft being slidable with respect to said base between first and second positions;
a plate having an aperture, said plate being pivotably connected to said shaft, such that when said shaft is in said first position said plate is in a position for locking to an implant, and when said shaft is slid to said second position, said plate pivots to a position for accepting insertion of a part of an implant;
a sleeve at least partially surrounding said shaft and being slidable along said shaft and slidable with respect to said base and said plate; and
wherein said shaft includes an elongated portion and a plunger portion connected to each other.

21. The apparatus of claim 20, wherein said elongated portion includes a tongue and said plunger portion includes a groove, and said tongue is at least partially within said groove.

22. The apparatus of claim 20, further comprising at least one spring abutting said plunger to bias said plunger toward said relatively forward end of said base.

23. The apparatus of claim 20, further comprising at least two springs abutting said plunger to bias said plunger toward said relatively forward end of said base.

24. The apparatus of claim 23, wherein said springs are substantially concentric.

25. An apparatus for connecting to an orthopedic implant, comprising:
a base having a relatively forward end and a relatively rearward end;
a shaft connected to said base, said shaft being slidable with respect to said base between first and second positions;
a plate having an aperture, said plate being pivotably connected to said shaft, such that when said shaft is in said first position said plate is in a position for locking to an implant, and when said shaft is slid to said second position, said plate pivots to a position for accepting insertion of a part of an implant;
a sleeve at least partially surrounding said shaft and being slidable along said shaft and slidable with respect to said base and said plate; and
wherein said base comprises an upper base portion and a lower base portion connected together.

26. The apparatus of claim 25, further comprising a closure connected to said upper base portion and said lower base portion, wherein closing said closure holds said base portions together, and opening said closure allows separation of at least a part of said upper base portion from at least a part of said lower base portion.

27. The apparatus of claim 26, wherein said closure includes a latch.

28. The apparatus of claim 26, wherein said base portions are pivotably connected, whereby opening said closure allows said base portions to pivot with respect to each other.

29. The apparatus of claim 25, wherein said base portions are pivotably connected together.

30. An apparatus for use in orthopedic surgery, comprising:
an orthopedic implant;
a plate member having first and second edges substantially opposite each other and an aperture extending entirely through said plate member;
a shaft connected to said plate member adjacent said first edge of said plate member, said shaft being movable to pivot said plate member substantially around said second edge of said plate;
a sleeve slidable with respect to said shaft; and
a base connected to said shaft,
wherein said aperture is sized to allow insertion of at least part of the orthopedic implant, and wherein said plate member has a first position in which said aperture is relatively open and such insertion can be accomplished with the orthopedic implant positioned within said aperture and extending through said plate member, and a second position in which said aperture is relatively closed and an inner surface of said aperture in said plate is in contact with the orthopedic implant.

31. The apparatus of claim 30, further comprising a stock connected to said base.

32. The apparatus of claim 30, wherein said base comprises an upper base portion and a lower base portion connected together.

33. The apparatus of claim 30, wherein said plate includes a roughened surface adjacent said aperture.

34. The apparatus of claim 30, wherein said second edge of said plate includes a rounded surface that facilitates pivoting of said plate.

35. The apparatus of claim 30, wherein said sleeve includes an end portion adapted to contact at least one of the group consisting of a spinal rod, an orthopedic connector, and an orthopedic plate.

36. An apparatus for use in orthopedic surgery, comprising:
a plate member having first and second edges substantially opposite each other and an aperture;
a shaft connected to said plate member adjacent said first edge of said plate member, said shaft being movable to pivot said plate member substantially around said second edge of said plate;
a sleeve slidable with respect to said shaft;
a base connected to said shaft;
an actuator movably connected to said base, said actuator operating said ratchet mechanism when said actuator is moved relative to said base; and
wherein said aperture is sized to allow insertion of at least part of an orthopedic implant, and wherein said plate member has a first position in which said aperture is relatively open and such insertion can be accomplished, and a second position in which said aperture is relatively closed and said plate can contact the orthopedic implant.

37. An apparatus for use in orthopedic surgery, comprising:
a plate member having first and second edges substantially opposite each other and an aperture;
a shaft connected to said plate member adjacent said first edge of said plate member, said shaft being movable to pivot said plate member substantially around said second edge of said plate;
a sleeve slidable with respect to said shaft;
a base connected to said shaft;
a stock connected to said base;
a first leaf spring connected to said actuator and a second leaf spring connected to said stock, wherein said leaf springs are connected together so as to bias the actuator and stock apart; and
wherein said aperture is sized to allow insertion of at least part of an orthopedic implant, and wherein said plate member has a first position in which said aperture is relatively open and such insertion can be accomplished, and a second position in which said aperture is relatively closed and said plate can contact the orthopedic implant.

38. An apparatus for use in orthopedic surgery, comprising:
a plate member having first and second edges substantially opposite each other and an aperture;
a shaft connected to said plate member adjacent said first edge of said plate member, said shaft being movable to pivot said plate member substantially around said second edge of said plate;
a sleeve slidable with respect to said shaft;
a base connected to said shaft, wherein said base comprises an upper base portion and a lower base portion connected together and wherein said base portions are pivotably connected together; and
wherein said aperture is sized to allow insertion of at least part of an orthopedic implant, and wherein said plate member has a first position in which said aperture is relatively open and such insertion can be accomplished, and a second position in which said aperture is relatively closed and said plate can contact the orthopedic implant.

39. The apparatus of claim 38, further comprising a closure connected to said upper base portion and said lower base portion, wherein closing said closure holds said base portions together, and opening said closure allows separation of at least a part of said upper base portion from at least a part of said lower base portion.

40. The apparatus of claim 39, wherein opening said closure allows said base portions to pivot with respect to each other.

41. The apparatus of claim 39, wherein said closure includes a latch.

42. An apparatus for use in orthopedic surgery, comprising:
a plate member having first and second edges substantially opposite each other and an aperture extending entirely through said plate member, said aperture including an inner circular surface; and
a shaft connected to said plate member adjacent said first edge of said plate member, said shaft being movable to pivot said plate member substantially around said second edge of said plate,
wherein said aperture is sized to allow insertion of at least part of an orthopedic implant, and wherein said plate member has a first position in which said aperture is relatively open and such insertion can be accomplished, and a second position in which said aperture is relatively closed and said plate can contact the orthopedic implant, and wherein said inner circular surface of said aperture of said plate is at least partially tapered.

43. An apparatus for use in orthopedic surgery, comprising:
a plate member having first and second edges substantially opposite each other and an aperture; and
a shaft connected to said plate member adjacent said first edge of said plate member, said shaft being movable to pivot said plate member substantially around said second edge of said plate,
wherein said aperture is sized to allow insertion of at least part of an orthopedic implant, and wherein said plate member has a first position in which said aperture is relatively open and such insertion can be accomplished, and a second position in which said aperture is relatively closed and said plate can contact the orthopedic implant, and wherein said aperture of said plate is at least partially tapered, and wherein said aperture of said plate has a constant diameter section.

44. An apparatus for use in orthopedic surgery, comprising:
a plate member having first and second edges substantially opposite each other and an aperture; and
a shaft connected to said plate member adjacent said first edge of said plate member, said shaft being movable to pivot said elate member substantially around said second edge of said plate,
wherein said aperture is sized to allow insertion of at least part of an orthopedic implant, and wherein said plate member has a first position in which said aperture is relatively open and such insertion can be accomplished, and a second position in which said aperture is relatively closed and said plate can contact the orthopedic implant, and wherein said aperture of said plate is at least partially tapered, and wherein said aperture of said plate is uniformly tapered.

45. An apparatus for use in orthopedic surgery, comprising:
a plate member having first and second edges substantially opposite each other and an aperture; and
a shaft connected to said plate member adjacent said first edge of said plate member, said shaft being movable to pivot said plate member substantially around said second edge of said plate,
wherein said aperture is sized to allow insertion of at least part of an orthopedic implant, and wherein said plate member has a first position in which said aperture is relatively open and such insertion can be accomplished, and a second position in which said aperture is relatively closed and said plate can contact the orthopedic implant, and wherein said plate includes a rounded surface and said shaft includes an indentation, and said indentation and said rounded surface are adjacent each other.

46. An apparatus for use in orthopedic surgery, comprising:
a plate member having first and second edges substantially opposite each other and an aperture; and
a shaft connected to said plate member adjacent said first edge of said plate member, said shaft being movable to pivot said plate member substantially around said second edge of said plate,
wherein said aperture is sized to allow insertion of at least part of an orthopedic implant, and wherein said plate member has a first position in which said aperture is relatively open and such insertion can be accomplished, and a second position in which said aperture is relatively closed and said plate can contact the orthopedic implant, and wherein said shaft includes an elongated portion and a plunger portion connected to each other.

47. The apparatus of claim 46, wherein said elongated portion includes a tongue and said plunger portion includes a groove, and said tongue is at least partially within said groove.

48. The apparatus of claim 46, further comprising at least one spring abutting said plunger to bias said plunger toward said relatively forward end of said base.

49. The apparatus of claim 46, further comprising at least two springs abutting said plunger to bias said plunger toward said relatively forward end of said base.

50. The apparatus of claim 49, wherein said springs are substantially concentric.

51. An apparatus for use in orthopedic surgery, comprising:
a plate member having first and second edges substantially opposite each other and an aperture;
a shaft connected to said plate member adjacent said first edge of said plate member, said shaft being movable to pivot said plate member substantially around said second edge of said plate; and
a lever connected to said shaft, wherein operating said lever causes said shaft to move, thereby pivoting said plate, and wherein said aperture is sized to allow insertion of at least part of an orthopedic implant, and wherein said plate member has a first position in which said aperture is relatively open and such insertion can be accomplished, and a second position in which said aperture is relatively closed and said plate can contact the orthopedic implant.

52. An apparatus for use in orthopedic surgery, comprising:
a plate member having first and second edges substantially opposite each other and an aperture;
a shaft connected to said plate member adjacent said first edge of said plate member, said shaft being movable to pivot said plate member substantially around said second edge of said plate; and
a slider connected to said shaft, wherein operating said slider causes said shaft to move, thereby pivoting said plate, and wherein said aperture is sized to allow insertion of at least part of an orthopedic implant, and wherein said plate member has a first position in which said aperture is relatively open and such insertion can be accomplished, and a second position in which said aperture is relatively closed and said plate can contact the orthopedic implant.

53. An apparatus for use in orthopedic surgery, comprising:
a plate member having first and second edges substantially opposite each other and an aperture;
a shaft connected to said plate member adjacent said first edge of said plate member, said shaft being movable to pivot said plate member substantially around said second edge of said plate;
a sleeve slidable with respect to said shaft;
a ratchet mechanism operable to move said sleeve with respect to said shaft and said plate; and
a base connected to said shaft,
wherein said aperture is sized to allow insertion of at least part of an orthopedic implant, and wherein said plate member has a first position in which said aperture is relatively open and such insertion can be accomplished, and a second position in which said aperture is relatively closed and said plate can contact the orthopedic implant.

54. The apparatus of claim 53 further comprising a stop connected to said base, said stop having at least one position connected to said ratchet mechanism in which movement in a rearward direction of said sleeve is limited, and a position disengaged from said ratchet mechanism so that said sleeve can be moved in a rearward direction.

55. The apparatus of claim 54, wherein said stop comprises at least one pawl that is pivotable between said at least one position connected to said ratchet mechanism and said position disengaged from said ratchet mechanism.

56. The apparatus of claim 55 wherein said stop comprises two pawls capable of operating independently of each other.

57. The apparatus of claim 55 wherein said stop comprises three pawls capable of operating independently of each other.

58. The apparatus of claim 57 wherein said pawls are nested.

* * * * *

UNITED STATES PATENT AND TRADEMARK OFFICE
CERTIFICATE OF CORRECTION

PATENT NO.       : 7,611,517 B2
APPLICATION NO. : 10/789610
DATED            : November 3, 2009
INVENTOR(S)      : Roy K. Lim It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1176 days.

Signed and Sealed this

Twelfth Day of October, 2010

David J. Kappos
*Director of the United States Patent and Trademark Office*